(12) United States Patent
Doi

(10) Patent No.: US 7,795,443 B2
(45) Date of Patent: Sep. 14, 2010

(54) COMPOUND AND ORGANIC THIN FILM TRANSISTOR

(75) Inventor: Noriyuki Doi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 215 days.

(21) Appl. No.: 12/048,446

(22) Filed: Mar. 14, 2008

(65) Prior Publication Data

US 2008/0241594 A1    Oct. 2, 2008

(30) Foreign Application Priority Data

Mar. 27, 2007    (JP) .............................. 2007-082479

(51) Int. Cl.
*C07D 417/10*    (2006.01)
(52) U.S. Cl. ........................................ 548/202; 254/40
(58) Field of Classification Search ................ 548/202, 548/206; 254/40
See application file for complete search history.

(56) References Cited

FOREIGN PATENT DOCUMENTS

JP    2004-107257 A    4/2004

OTHER PUBLICATIONS

Hong Meng et al., "High-Performance, Stable Organic Thin-Film Field-Effect Transistors Based on Bis-5'- alkylthiophen-2'-yl-2,6-anthracene Semiconductors," 127(8) J. Am. Chem. Soc. 2406-07 (no month, 2005) (with supplement).*

Jeffrey A. Merlo et al., "p-Channel Organic Semiconductors Based on Hybrid Acene-Thiophene Molecules for Thin-Film Transistor Applications," 127(11) J. Am. Chem. Soc. 3997-4009 (no month, 2005) (with supplement).*

X. Michael Hong et al., "Thiophene-Phenylene and Thiophene-Thiazole Oligomeric Semiconductors with High Field-Effect Transistor On/Off Ratios," 13(12) Chem. Mater. 4686-91 (Nov. 2001).*

Yen-Yi Lin et al., "Pentacene-Based Organic Thin-film Transistors," 44(8) IEEE Transactions on Electron Devices 1325-31 (Aug. 1997).*

* cited by examiner

*Primary Examiner*—Rebecca L Anderson
*Assistant Examiner*—Matthew P Coughlin
(74) *Attorney, Agent, or Firm*—Fitzpatrick, Cella, Harper & Scinto

(57) ABSTRACT

Provided are a compound represented by the following general formula (1):

A1-B1-X1-C1-D1 wherein A1 and D1 each represent an unsubstituted or substituted anthracene ring; B1 and C1 each represent an unsubstituted or substituted thiazole ring; and X1 represents a single bond or a divalent group, and an organic thin film transistor using the compound.

3 Claims, 1 Drawing Sheet

COMPOUND AND ORGANIC THIN FILM TRANSISTOR

BACKGROUND OF THE INVENTION

1. Field of the Invention

The present invention relates to a novel compound and an organic thin film transistor.

2. Description of the Related Art

An organic thin film transistor (hereinafter, referred to as an organic TFT) using an organic material for an active layer has excellent processability compared with that of inorganic materials such as crystalline silicon and amorphous silicon, and has been actively investigated toward the realization of low-cost devices. Even when an organic semiconductor material is used for an organic TFT, a value of field effect mobility of the organic TFT comparable to that of an amorphous silicon TFT has been recently reported. Therefore, an organic TFT has been expected to have practical application as a driving transistor of a display and the like (See IEEE Transactions on Electron Devices, 44, 1325 (1997)). However, an organic TFT generally has a low field effect mobility compared with that of an inorganic TFT. Thus, it is desirable to develop an organic semiconductor material having a higher field effect mobility for practical applications.

Examples of an organic semiconductor material recently developed include a thiophene-phenylene oligomer, a thiophene-thiazole oligomer (see Chem. Mater., 13, 4686 (2001)), a compound having two molecules of thiophene bound to anthracene (see J. AM. CHEM. SOC., 2005, 127, pp. 2406 to 2407, and J. AM. CHEM. SOC., 2005, 127, pp. 3997 to 4009) and an anthracene oligomer (see Japanese Patent Application Laid-Open No. 2004-107257). These organic semiconductor materials have a relatively high field effect mobility, but are not sufficient for practical applications.

The present invention has been made in view of such a related art, and provides an organic TFT achieving a high field effect mobility and a novel compound capable of forming an organic semiconductor layer of the organic TFT.

SUMMARY OF THE INVENTION

The present invention provides a compound represented by the following general formula (1).

General Formula (1)

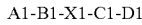

wherein A1 and D1 each represent an unsubstituted or substituted anthracene ring; B1 and C1 each represent an unsubstituted or substituted thiazole ring; and X1 represents a single bond or a divalent group.

The compound represented by the above-mentioned general formula (1) may preferably be a compound represented by the following general formula (2).

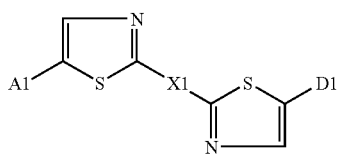
General Formula (2)

wherein A1 and D1 each represent an unsubstituted or substituted anthracene ring; and X1 represents a single bond or a divalent group.

Further, the compound represented by the above-mentioned general formula (1) may preferably be a compound represented by the following general formula (3).

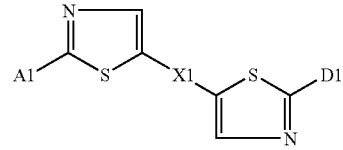
General Formula (3)

wherein A1 and D1 each represent an unsubstituted or substituted anthracene ring; and X1 represents a single bond or a divalent group.

In the above-mentioned general formulas (1) to (3), the X1 may preferably be a divalent group containing at least one benzene ring or a divalent group containing at least one thiophene ring. The X1 may preferably be an unsubstituted or substituted naphthalene ring.

An organic TFT may preferably contain in an organic semiconductor layer (active layer) a compound represented by any one of the above-mentioned general formulas (1) to (3).

Further features of the present invention will become apparent from the following description of exemplary embodiments with reference to the attached drawings.

DESCRIPTION OF THE EMBODIMENTS

Figure 1:
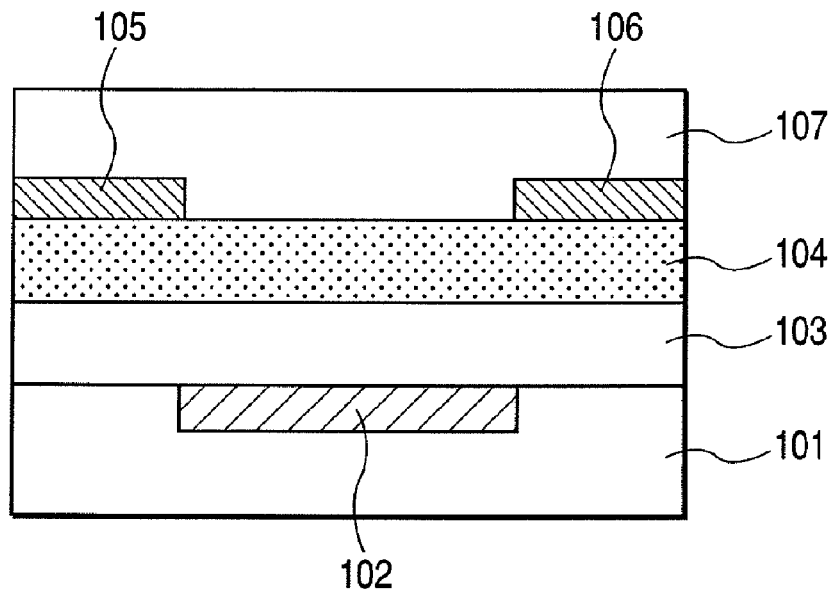
FIG. 1 is a cross-sectional view illustrating an example of a structure of a top-contact type organic TFT.

Hereinafter, the present invention is described in detail. A compound of the present invention is represented by the following general formula (1).

General Formula (1)

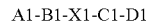

wherein B1 and C1 each represent an unsubstituted or substituted thiazole ring.

Examples of the compound of the general formula (1), wherein B1 and C1 are unsubstituted thiazole rings are represented by the following general formulas (2) and (3).

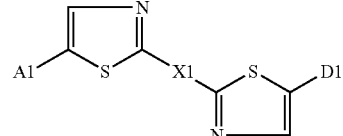
General Formula (2)

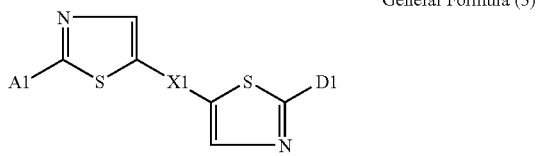

General Formula (3)

In the general formulas (1) to (3), A1 and D1 each represent an unsubstituted or substituted anthracene ring.

X1 represents a single bond or a divalent group. That is, X1 represents a divalent binding group for binding two thiazole rings (B1 and C1) by a conjugate bond and a case of directly binding two thiazole rings is also included. Specific examples of X1 include binding groups having, as a skeleton, aromatic hydrocarbon rings such as benzene, naphthalene, anthracene, tetracene, pentacene, pyrene, phenanthrene and fluorene rings; aromatic heterocyclic rings such as furan, thiophene, pyrrole, oxazole, thiazole, imidazole, pyrazole, benzofuran, benzothiophene, benzothiazole and carbazole rings; alkenes such as ethylene and butadiene; and alkynes such as acetylene and diacetylene. In addition, divalent binding groups formed by a combination of the skeletons can also be used.

In the above-mentioned general formulas (1) to (3), the X1 may preferably be a divalent group containing at least one benzene ring or a divalent group containing at least one thiophene ring.

When an organic semiconductor material is used as P-type semiconductor, a hole injection from the electrode is facilitated by forming an HOMO (Highest occupied molecular orbital) of a molecule near work function of a metal used for a source/drain electrode, and the performance is improved. In a case of using the organic semiconductor material of the present invention, for improvement of field effect mobility, when X1 is regarded as a molecule, X1 preferably has an HOMO value larger than that of benzene except for when two thiazole rings are directly bound to each other (when X1 is a single bond).

In the general formula (1), anthracene rings represented by A1 and D1, thiazole rings represented by B1 and C1, and a divalent group represented by X1 for binding two thiazole rings by a conjugate bond may be unsubstituted or substituted. Specific examples of the substituent include halogen atoms such as a fluorine atom, a chlorine atom and bromine atom, chain alkyl groups such as a methyl group, an ethyl group, a propyl group, an isopropyl group, a butyl group, a tert-butyl group, a pentyl group, a hexyl group, an octyl group, a decyl group, a dodecyl group, a tridecyl group, a tetradecyl group, a pentadecyl group, a hexadecyl group and an octadecyl group, cyclic alkyl groups such as a cyclopentyl group and a cyclohexyl group, aryl groups such as a phenyl group, a tolyl group and a naphthyl group, aromatic heterocyclic groups such as a thienyl group and a furyl group, silyl groups such as a trimethylsilyl group, a triethylsilyl group, a triisopropylsilyl group, a tert-butyldimethylsilyl group, a triphenylsilyl group and a dimethylphenylsilyl group, alkoxy groups such as a methoxy group, an ethoxy group, a propyloxy group and a butyloxy group, and alkylthio groups such as a methylthio group, an ethylthio group, a propylthio group and a butylthio group. The alkyl groups, the aryl groups and the silyl groups may be each bound through an ethynyl group. Further, these substituents may be further substituted by the above-mentioned substituents. The thiazole ring can bind an anthracene ring at one of 2-, 4- and 5-positions of the thiazole ring, but preferably binds an anthracene ring at one of 2- and 5-positions of the thiazole ring. In addition, the thiazole ring may form a condensed ring with other ring.

The compound represented by the above-mentioned general formula (1) can be used as an organic semiconductor material. As such an organic semiconductor material, a polymer having a structure of the general formula (1) as a constitutional unit can also be used.

Specific examples of the compound represented by the general formula (1) are shown below by structural formulas, but the present invention is not limited to these compounds.

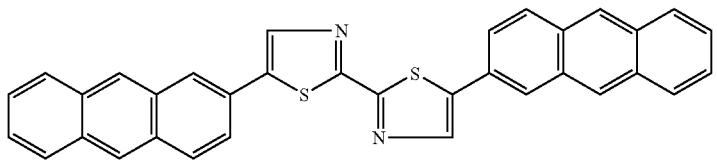

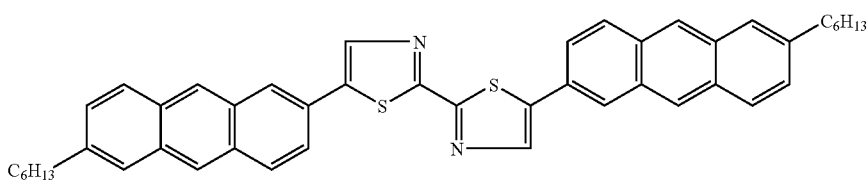

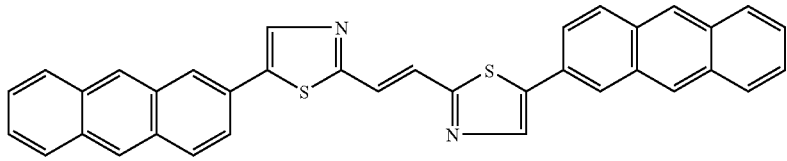

-continued
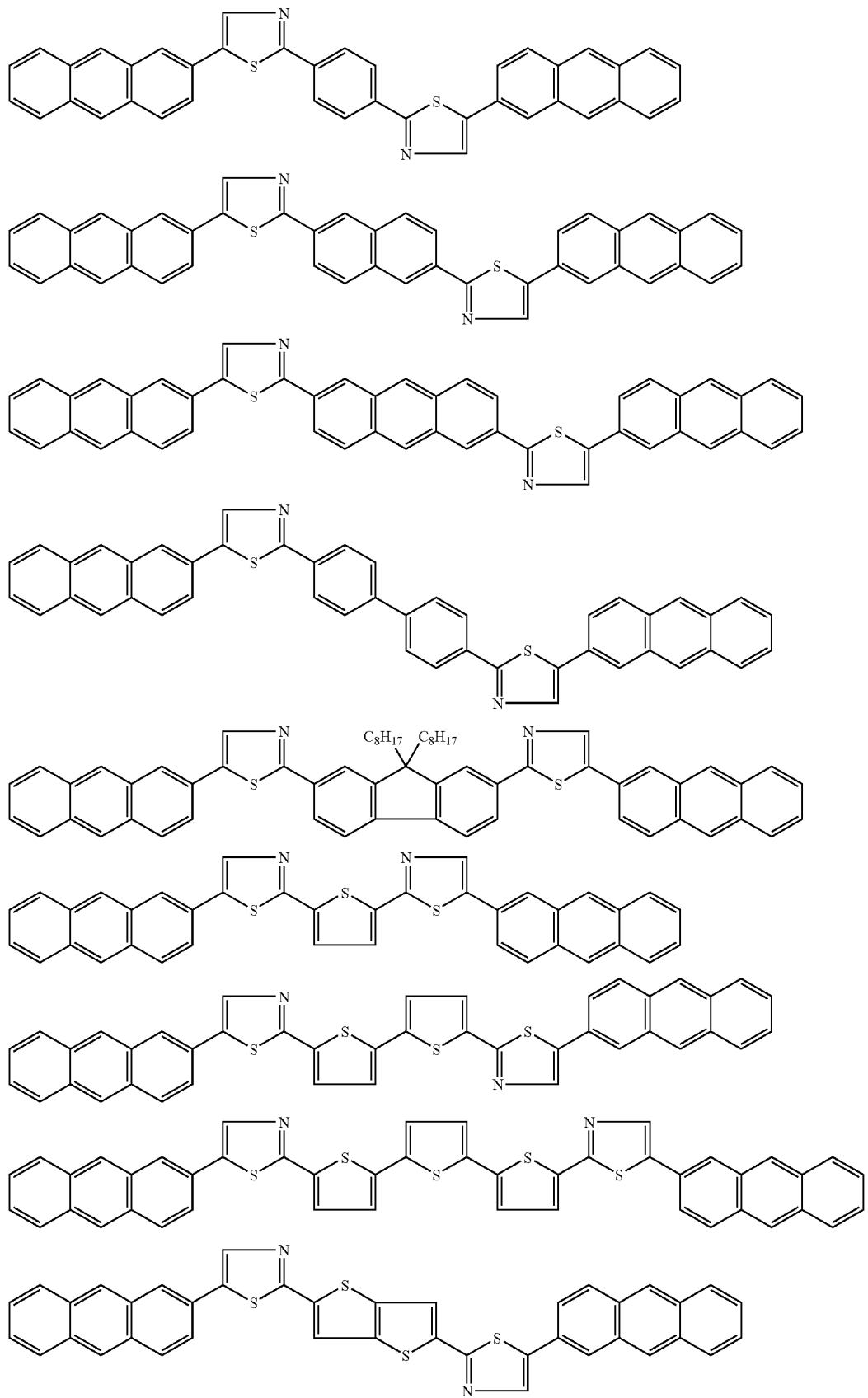

-continued
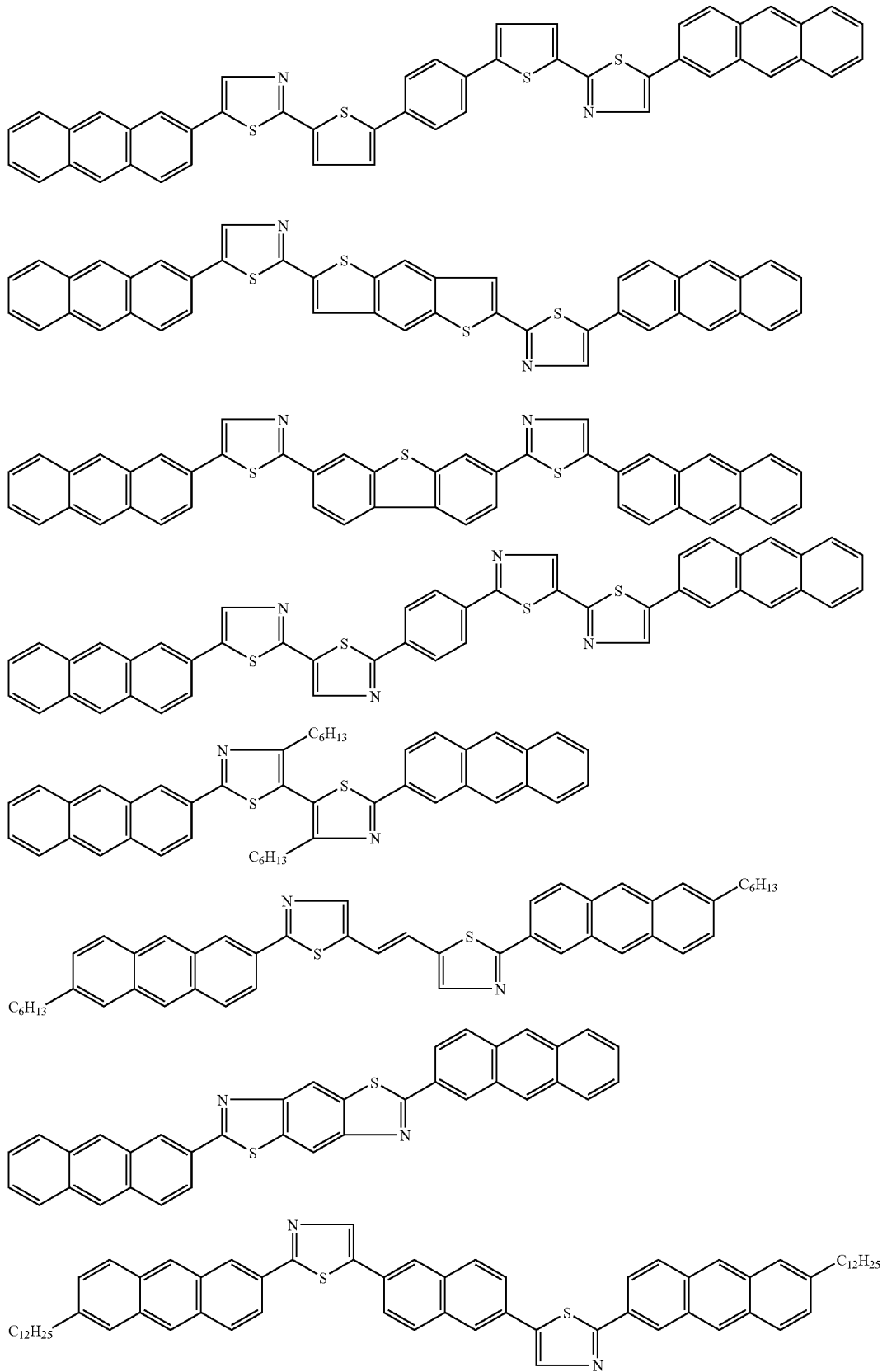

-continued

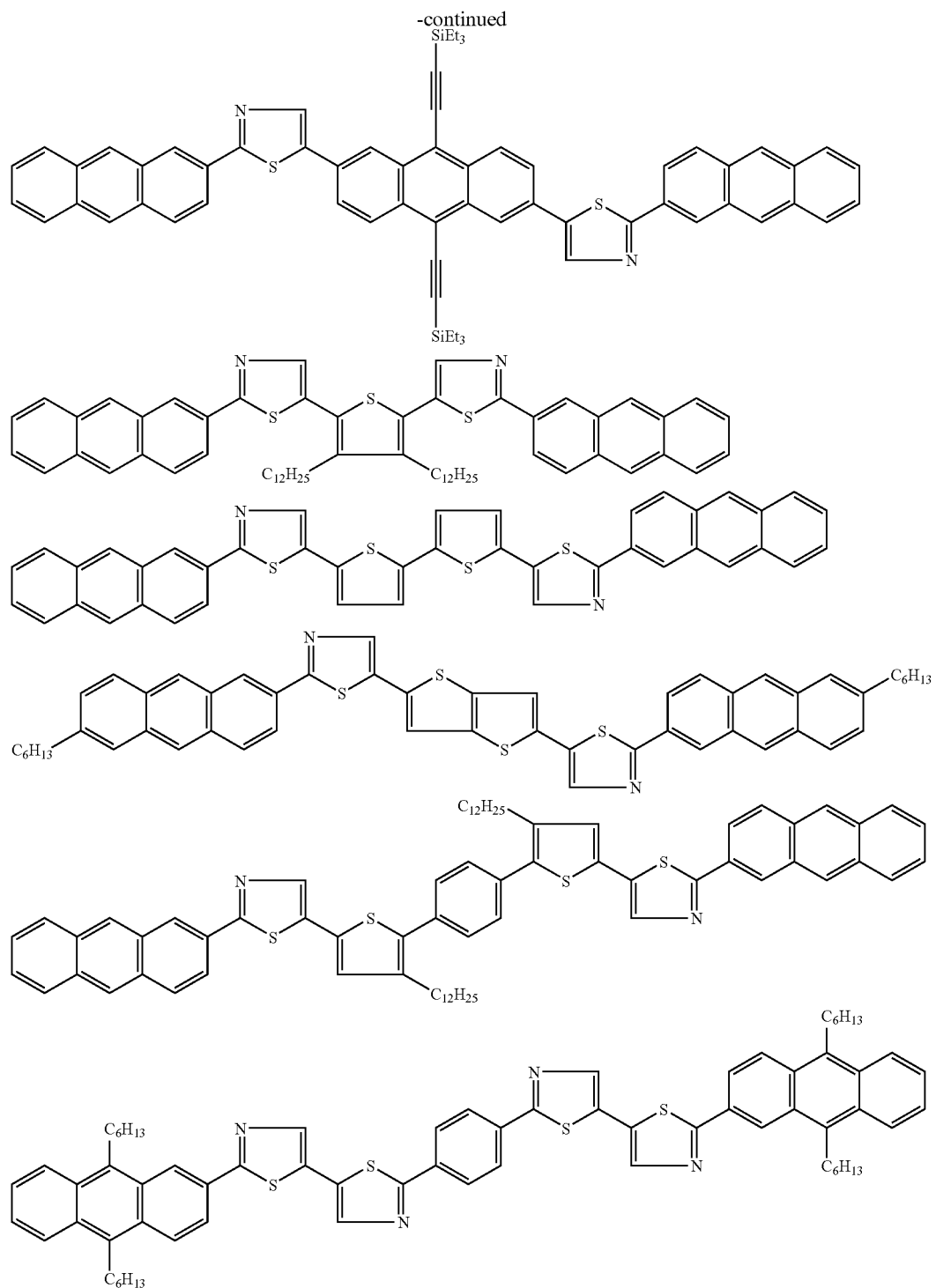

As synthesis methods of these compounds, a general cross-coupling method is employed. Specific examples of the cross-coupling method include Suzuki coupling, Stille coupling, Negishi coupling and Tamao coupling. Suzuki coupling may preferably be employed from the viewpoint of hazardous properties of reagents to be used. In the case of Suzuki coupling, a compound having a boronic acid group or a boronate ester group, and a compound having a halogen atom or a pseudohalogen compound are subjected to coupling reaction in the presence of a base using a palladium catalyst, and thereby a target product can be obtained. The organic semiconductor material of the present invention can be purified by a general purification method such as column chromatography, recrystallization and sublimation to improve the purity.

Next, an example of the organic TFT of the present invention will be described.

Figure 2:
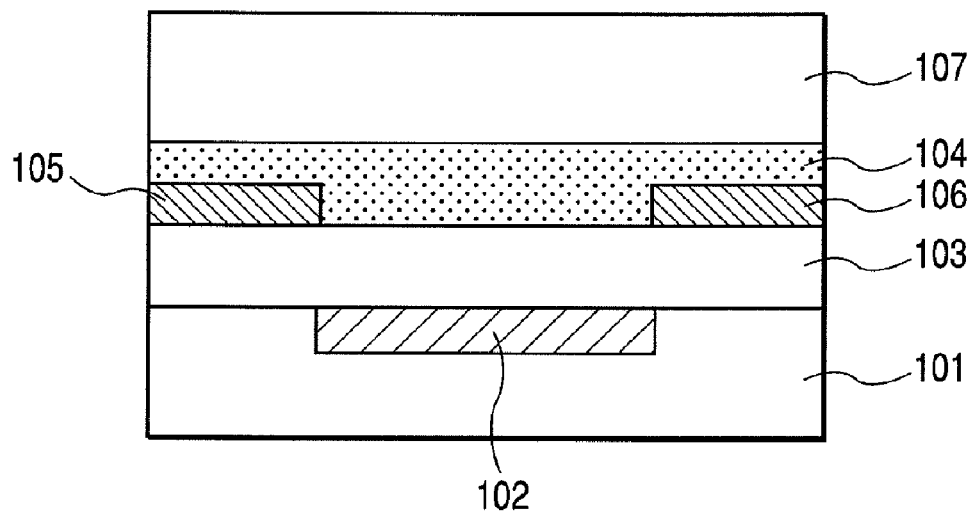
FIG. 2 is a cross-sectional view illustrating an example of a structure of a bottom-contact type organic TFT.

The structure of the organic TFT of the present invention can be made to, for example, a top-contact type illustrated in FIG. 1 and a bottom-contact type illustrated in FIG. 2. In drawings, 101 denotes a substrate, 102 denotes a gate electrode, 103 denotes a gate insulating film, 104 denotes an organic semiconductor layer, 105 denotes a source electrode, 106 denotes a drain electrode and 107 denotes a protection layer.

The substrate 101 can be selected from various organic and inorganic materials, and specific examples thereof include inorganic materials such as silicon, aluminum, glass, alumina sintered product and stainless steel, organic materials such as polyethylene terephthalate, polyethylene naphthalate, polyimide, polyethylene, polypropylene, polyetheretherketone, polysulfone and polyphenylene sulfide, and a composite material like an organic material reinforced by glass fiber.

Materials of the gate electrode 102, the source electrode 105 and the drain electrode 106 are selected from conductive materials. Specific examples of such conductive materials include metal materials such as gold, platinum, copper, silver, palladium, chromium, molybdenum, titanium, nickel and aluminum, nonmetallic inorganic materials such as tin oxide, indium oxide and indium tin oxide, organic materials such as polythiophene and polyaniline, and carbon materials. An alloy can also be used as a metal material. In addition, in the case of using a conductive material as a substrate, the substrate can be used as a gate electrode.

Examples of the materials of the gate insulating film 103 include inorganic materials such as silicon oxide, silicon nitride, alumina, tantalum oxide, organic materials such as polymethyl methacrylate, polyimide, polyparaxylylene, polyvinyl alcohol and polyvinyl phenol, and silicon materials such as polymethylsilsesquioxane. Further, the gate insulating film may have a laminated structure made of a plurality of layers.

The organic semiconductor layer 104 is a layer containing the novel compound of the present invention described above.

The protection layer 107 is formed for the purpose of preventing deterioration of an organic TFT. The material for the protection layer 107 is not particularly limited, but generally includes polyparaxylylene, an epoxy resin and a silicone resin. These materials can be used also as a composite material in combination with inorganic materials such as silicon oxide, silicon nitride and aluminum. The protection layer may be omitted.

A gate electrode, a gate insulating film, an organic semiconductor, and source and drain electrodes of the organic TFT are formed by known methods. Specific examples of the methods include printing methods such as a screen printing method, an offset printing method and an inkjet printing method, a spin coating method, a dip coating method, a spray coating method, a vacuum vapor deposition method, a sputtering method and a plasma CVD method. Pattern processing can also be performed by, for example, use of a shadow mask and a method of combining existing photolithography and etching.

EXAMPLES

Hereinafter, the present invention will be described in detail by means of examples, but should not be limited to these examples.

Example 1

(Synthesis of Organic Semiconductor Material)

The following compounds (1) and (2) were synthesized by methods of the following reaction formulas (1-1) and (2-1), respectively, and were used for next coupling. As a result, a compound (3) that is an example of a compound in which A1 and D1 are each an unsubstituted anthracene ring and X1 is an unsubstituted naphthalene ring in the general formula (1) was obtained.

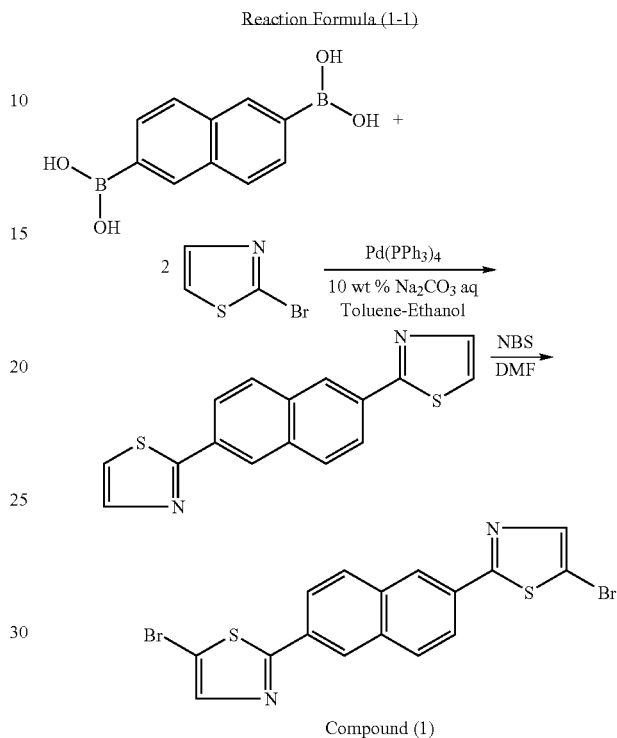

Reaction Formula (1-1)

Compound (1)

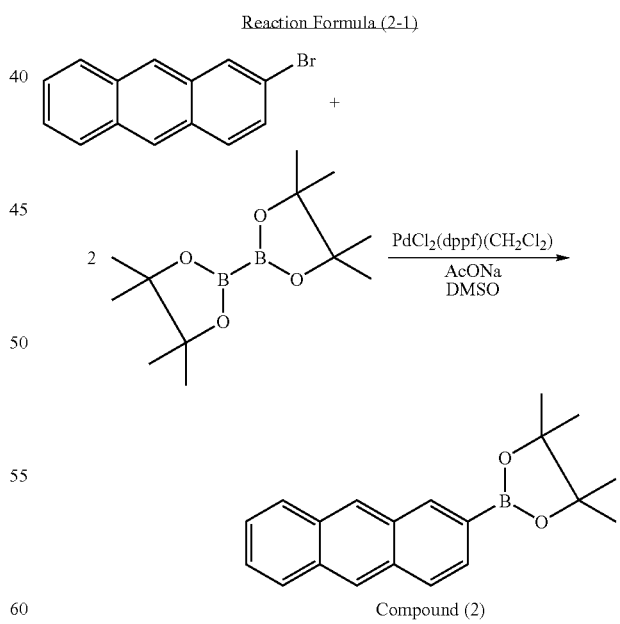

Reaction Formula (2-1)

Compound (2)

In a nitrogen-purged reactor were placed 60 mL of toluene, 30 mL of ethanol, 30 mL of a 10 wt % sodium carbonate aqueous solution, 150.2 mg (0.13 mmol) of tetrakis(triphenylphosphine)palladium, and 494.3 mg (1.1 mmol) of the compound (1) and 1.0731 g (3.5 mmol) of the compound (2)

which had been previously prepared, and bubbling was performed with Ar gas for several minutes in order to remove oxygen remaining in the system. The reaction mass was heated by a temperature-controlled heating medium and refluxed for 24 hours. After cooling the reaction mass to room temperature, precipitated crystals were filtered off and the crystals collected by filtration were sufficiently washed sequentially with pure water, ethanol and toluene. The crystals were dried under vacuum, and thereby 450.2 mg (1.58 mmol) of yellow crystals of a compound (3) were obtained in a yield of 89%.

MALDI-TOF m/z=646.99 (calc. 646.15)

The temperature of the substrate was set to 140° C. and the compound (3) was vapor-deposited so as to form a film with a thickness of about 40 nm (400 angstroms) while monitoring the film thickness by a quartz resonator, and thereby an organic semiconductor layer was formed. Finally, a source electrode and a drain electrode (a gate length of 50 μm to 100 μm, a gate width of 3 mm to 6 mm) were formed by vacuum vapor deposition of gold using a shadow mask, and thereby an organic TFT was produced. The silicon substrate was used also as a gate electrode and the silicon oxide film was used as a gate insulating film. Property of the organic TFT was evaluated using a parameter analyzer, and as a result, the field effect mobility was 0.2 cm²/Vs. The result is shown in Table 1.

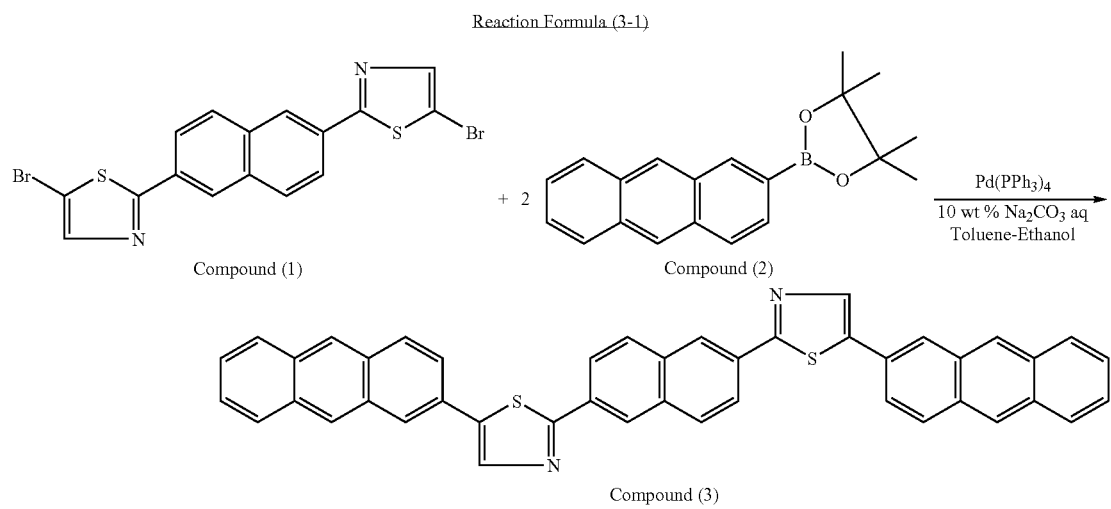

Reaction Formula (3-1)

Example 2

(Preparation and Property Evaluation of Organic TFT)

A highly doped silicon substrate having a silicon oxide film with a thickness of 500 nm was prepared, and this substrate was immersed in acetone for electronics industry and was subjected to ultrasonic cleaning for 3 minutes. Subsequently, the substrate was similarly subjected to ultrasonic cleaning with pure water for 3 minutes, and water content adhered to the substrate was blown off by nitrogen gas and dried.

Comparative Example 1

A device was produced in the same manner as in Example 2, except the following compound (4) was used as an organic semiconductor material and the temperature of the substrate was set to 100° C. A property of the device was evaluated using a parameter analyzer. As a result, the field effect mobility was 0.12 cm²/Vs. This is shown in Table 1.

TABLE 1

| | Organic TFT material | Field effect mobility |
|---|---|---|
| Example 2 | Compound (3) | 0.2 cm²/Vs |
| Comparative Example 1 | Compound (4) | 0.12 cm²/Vs |

(Note 1)
Field effect mobility is a value measured under the conditions of a drain voltage of −100 V (constant) and a gate voltage of −100 V to +20 V (sweep).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-082479, filed Mar. 27, 2007, which is hereby incorporated by reference herein in its entirety.

What is claimed is:

1. A compound represented by formula (1):

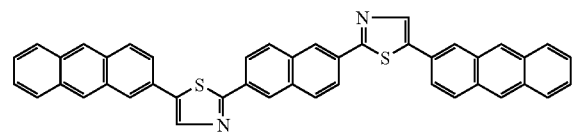

(1)

2. An organic thin film transistor comprising a gate electrode, a gate insulating film, an organic semiconductor layer, a source electrode, and a drain electrode, wherein the organic semiconductor layer contains the compound according to claim 1.

3. The organic thin film transistor according to claim 2, wherein the organic semiconductor layer is disposed on the gate insulating film and the source electrode and the drain electrode are disposed on the organic semiconductor layer.

* * * * *